(12) United States Patent
Ferreira Soto et al.

(10) Patent No.: US 11,826,391 B2
(45) Date of Patent: Nov. 28, 2023

(54) ANTIBACTERIAL FORMULATION COMPRISING A MIXTURE OF BACTERIOPHAGES; USE AND METHOD FOR PREVENTING OR TREATING DISEASES CAUSED BY SALMONELLA SPP. IN FARM ANIMALS BY ORAL ADMINISTRATION OF THE FORMULATION

(71) Applicant: PHAGELAB CHILE SPA, Santiago (CL)

(72) Inventors: Nicolas Ferreira Soto, Santiago (CL); Mauro Canaval Alfaro, Santiago (CL); Pablo Cifuentes Palma, Santiago (CL); Daniel Tichy Navarro, Santiago (CL); Maria Sofia Zamudio Canas, Santiago (CL); Matias Aguilera Barrios, Santiago (CL); Trinidad Pizarro Black, Vina del Mar (CL); Juan Sacre Ravera, Santiago (CL); Hans Pieringer Castro, Santiago (CL); Michael Pino Barrientos, Santiago (CL); Rodrigo Norambuena Venegas, Santiago (CL); Francisca Contreras Vera, Santiago (CL); Angelica Zavala Prati, Santiago (CL)

(73) Assignee: PHAGELAB CHILE SPA, Santiago (CL)

( * ) Notice: Subject to any disclaimer, the term of this patent is extended or adjusted under 35 U.S.C. 154(b) by 0 days.

(21) Appl. No.: 17/764,112

(22) PCT Filed: May 19, 2021

(86) PCT No.: PCT/CL2021/050044
§ 371 (c)(1),
(2) Date: Mar. 25, 2022

(87) PCT Pub. No.: WO2022/241579
PCT Pub. Date: Nov. 24, 2022

(65) Prior Publication Data
US 2023/0270801 A1  Aug. 31, 2023

(51) Int. Cl.
*A61K 35/76* (2015.01)
*A61P 31/04* (2006.01)
*A01N 63/40* (2020.01)
*A01P 1/00* (2006.01)

(52) U.S. Cl.
CPC ............. *A61K 35/76* (2013.01); *A01N 63/40* (2020.01); *A01P 1/00* (2021.08); *A61P 31/04* (2018.01)

(58) Field of Classification Search
CPC ............. A01N 63/40; A01P 1/00; A61P 31/04
See application file for complete search history.

(56) References Cited

U.S. PATENT DOCUMENTS

| 2010/0158870 A1 | 6/2010 | Kang et al. |
| 2019/0070231 A1 | 3/2019 | Florez |
| 2021/0046131 A1 | 2/2021 | Pan et al. |

FOREIGN PATENT DOCUMENTS

| EP | 2750519 B1 | 1/2016 |
| JP | 6112961 B2 | 4/2017 |
| WO | 2013014273 A1 | 1/2013 |

OTHER PUBLICATIONS

Li, Zhiwei, et al. A broad-spectrum phage controls multidrug-resistant *Salmonella* in liquid eggs, Food Res Int. Jun. 2020; vol. 132, p. 109011.
International Search Report and Written Opinion for Corresponding International Application No. PCT/CL2021/050044 dated Feb. 18, 2022 and English translation (23 pages).
Muhsin Jamal, et al., "Bacteriophages: An Overview of the Control Strategies Against Multiple Bacterial Infections in Different Fields", Journal of Basic Microbiology, pp. 1-11, 2018.
A.P. Magiorakos, et al., "Multidrug-Resistant, Extensively Drug-Resistant and Pandrug-Resistant Bacteria: An International Expert Proposal for Interim Standard Definitions for Acquired Resistance", Clin Microbiol Infect, vol. 18, pp. 268-281, 2012.
Rajesh Modi, et al., "Effect of Phage on Survival of *Salmonella enteritidis* During Manufacture and Storage of Cheddar Cheese Made From Raw and Pasteurized Milk", Journal of Food Protection, vol. 64, No. 7, pp. 927-933, 2001.
Casandra W. Philipson, et al., Charaterizing Phage Genomes for Therapeutic Applications, Viruses, vol. 10, No. 188, pp. 1-20, 2018.
Jean M. Whichard, et al., "Suppression of *Salmonella* Growth by Wild-Type and Large-Plaque Variants of Bacteriophage Felix O1 in Liquid Culture and on Chicken Frankfurters", Journal of Food Protection, vol. 66, No. 2, pp. 220-225, 2003.

*Primary Examiner* — Janet L Andres
*Assistant Examiner* — Ruixue Wang
(74) *Attorney, Agent, or Firm* — Lucas & Mercanti, LLP

(57) ABSTRACT

An antibacterial formulation having a mixture of bacteriophages with lytic activity against strains of *Salmonella* spp. and a pharmaceutically and veterinarily acceptable vehicle, pH stabilizer and/or excipients. This formulation is for the prevention and treatment of infectious diseases caused by *Salmonella* spp. and different serovars; use and method for preventing or treating infectious diseases caused by *Salmonella* spp. in farm animals by administering the antibacterial formulation to a non-human animal orally.

15 Claims, 9 Drawing Sheets a)

b)

a)

b)

a)

b)

c)

a)

b)

…

Figure 1:
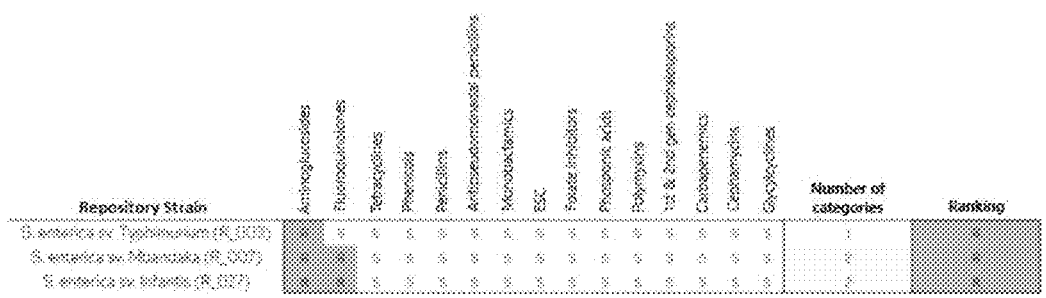
Figure 1:
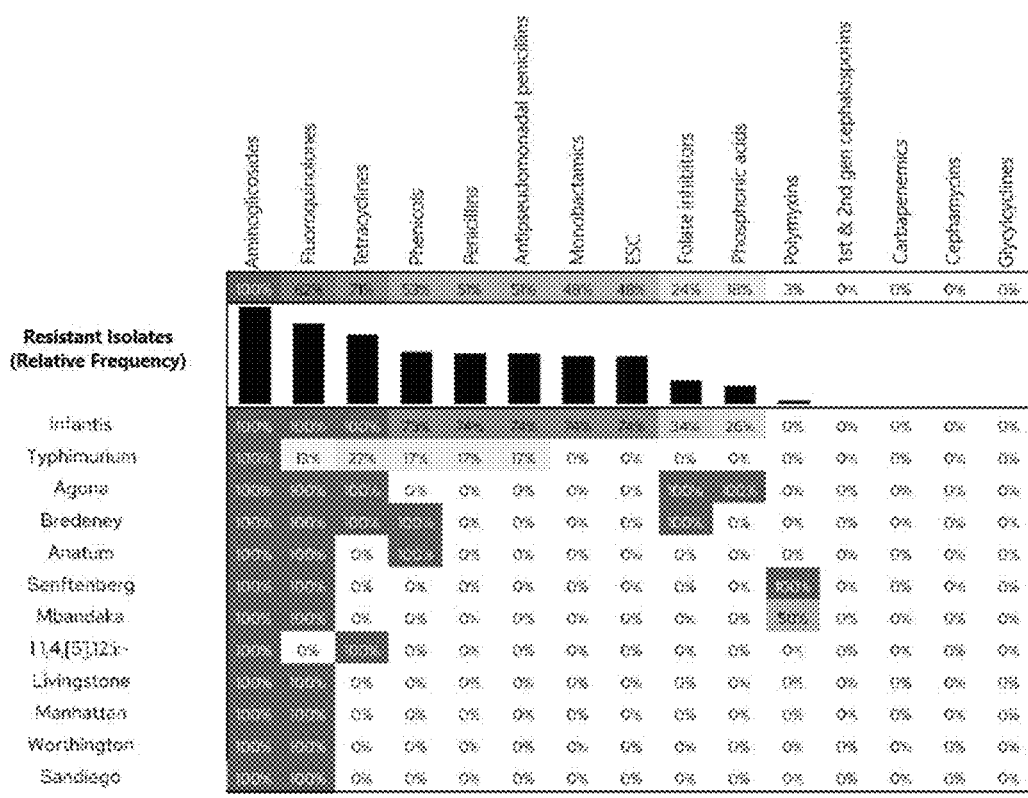

ANTIBACTERIAL FORMULATION COMPRISING A MIXTURE OF BACTERIOPHAGES; USE AND METHOD FOR PREVENTING OR TREATING DISEASES CAUSED BY SALMONELLA SPP. IN FARM ANIMALS BY ORAL ADMINISTRATION OF THE FORMULATION

CROSS REFERENCE TO RELATED APPLICATION

This Application is a 371 of PCT/CL2021/050044 filed on May 19, 2021, which is incorporated herein by reference.

FIELD OF INVENTION

The present invention refers to bacteriophages exhibiting lytic activity against pathogenic Enteriobacteriaceae, particularly of the *Salmonella* genus, their use in solutions for eliminating this pathogen and associated methods. The present invention describes a method of treatment and/or prevention of diseases caused by enterobacteria such as *Salmonella* by means of phage therapy for the reduction of the prevalence and bacterial load of *Salmonella* in the breeding, slaughter and processing stage of farm and/or breeding animals, particularly poultry. Also, it refers to a formulation comprising bacteriophages as a formulation in liquid form for disinfecting environments, surfaces and equipment, in particular, environments and surfaces.

BACKGROUND

The poultry industry has expanded around the world due to population growth, increased purchasing power and urbanization processes.

Breeding methods in the poultry industry have resulted in birds that respond for specialized purposes and are increasingly productive, which has caused the poultry industry to rapidly increase in size. However, this growth requires management by experts in the development and transfer of feeding, slaughtering, processing, safety and efficiency technologies that favor large-scale production chains.

One of the problems facing the poultry industry is diseases affecting poultry caused by pathogenic organisms. Diseases affecting these birds can have repercussions that can be devastating for productivity, production and in the trade of live birds, meat and other poultry products. The pathogens that affect these birds are zoonotic, therefore, they can affect human health. One of these zoonotic pathogens is *Salmonella*.

The disease caused by *Salmonella* infection, called *Salmonellosis*, is the main cause of human infections through food. According to data provided by the EU, the origin of *Salmonella* is mainly in animal species, particularly birds. With respect to zoonosis, the EU indicates that there are 5 specific *Salmonella* serovars: *S. enteritidis, S. typhimurium, S. infantis, S. hadar* and S. Virchow, which are related to laying hens and broilers.

In birds, *Salmonella* infection depends on three types of toxins which cause different physiological effects in birds. The toxins correspond to endotoxins that produce fever in birds and two enterotoxins, one that causes a cellular secretory response in the intestinal lumen and a toxin that causes structural damage to the intestinal cell mucosa. To this, one can add adherence to the intestinal epithelium, the ability to invade the mucosa and the ability of the bacterium to survive by replication within the cell. Infection can be acquired orally, intra cloacal, intratracheal, nasal, ocular and by aerosols. Infected birds can have persistent dissemination of the bacteria through feces, given intestinal colonization, facilitating horizontal transmission. Systemic dissemination multiplies the bacteria in liver, spleen, ovary, oviduct, blood, heart, testicles, yolk sac and peritoneum, among other organs. Conventional treatments to prevent *Salmonella* infection in poultry include vaccination, heat treatment of feed and/or incorporation of acids, frequent cleaning and disinfection, control and eradication of infestations such as mites and insects. In addition to not allowing the coexistence of other species or keeping them in separate places from the birds.

One form of treatment for *Salmonella* infection in chickens is the use of specific bacteriophages against this bacterium. These biological agents aim to eliminate the pathogenic bacteria colonizing the intestine of these animals while remaining harmless to the microbiota of the birds and to eukaryotic cells.

The use of bacteriophages as therapy attempts to reduce or eliminate the use and abuse of antibiotics and thus resolve the infection without generating resistance in bacteria.

Phages (or in this case bacteriophages) have the ability to recognize the surface of bacterial cells in a specific way, then introduce their genetic material inside the cell and multiply using the machinery of the cell, in this case the bacterium. After multiplying, phages can exit the bacterium by bacterial lysis and release of viral progeny into the environment. This is known as lytic replication, since they are quickly released from the host, making them suitable for use in therapeutic applications, unlike the lysogenic cycle phages which, when injecting their genetic material into the cell, remain in a state of latency.

Examples of this type of treatments for birds with bacteriophages can be found in Whichard et al. (2003); Modi et al. (2001) and Jamal et al. (2019). In these papers, the authors describe several analyses in which the antimicrobial capacity of bacteriophages as treatment and control strategies for infectious diseases, particularly those produced by *Salmonella*, is evaluated. They describe how bacteriophages can decrease the bacterial load or eliminate it completely in *Salmonella* strains such as *S. enteritidis, S. typhi* and *S. typhimurium*.

Evaluation results have also been reported that provide an industrial application to the use of bacteriophages for the elimination of *Salmonella*. For example, documents US2021046131A1, WO2013014273 (A1), describe the oral administration of bacteriophages in farm animals, particularly poultry for the prevention or elimination of infections caused by *Salmonella*. These documents present results in which the use of one or more bacteriophages or mixtures of bacteriophages present positive effects in the reduction of the *Salmonella* load in birds, mainly of *S. enteritidis* and *S. typhimurium* serovars.

Documents US2010158870A1, US2019070231A1, WO2013014273 (A1) present applications for the use of bacteriophage mixtures to eliminate the bacterial load of *Salmonella* in poultry pieces and on food handling surfaces, the results presented in these documents indicate that the use of these mixtures decreases the bacterial count.

DESCRIPTION OF INVENTION

The present invention relates to an antibacterial formulation comprising a mixture or combination of an effective amount of bacteriophages, which exhibit specific lytic activity against *Salmonella* spp. particularly exhibiting lytic activity against *Salmonella infantis, typhimurium*, Mbandaka, Worthington, Anatum, Livingstone, Manhattan, Bredeney, Agona, I1,4[5]),12:i:-, Sandiego serovars. More specifically, the present invention relates to an antibacterial formulation for veterinary use comprising a mixture of bacteriophages specific against *Salmonella* spp. serovars *infantis, typhimurium*, Mbandaka, Worthington, Anatum, Livingstone, Manhattan, Bredeney, Agona, I1,4[5]),12:i:-, Sandiego with a vehicle, pH stabilizer and/or pharmaceutical and veterinary acceptable excipients.

The bacteriophages comprising the formulation were identified and deposited in accordance with the requirements of the Budapest Treaty with the International Depositary Authority of Canada (IDAC, located at National Microbiology Laboratory, Public Health Agency of Canada, Canadian Science Center for Human and Animal Health, 1015 Arlington Street, Winnipeg, MVR3E 3R2) on Aug. 6, 2020. As set out in the original deposit certificates, the bacteriophages part of the composition of the present invention are identified as:

| | |
|---|---|
| Bacteriophage SenM-L8 | IDAC deposit 060820-01; |
| Bacteriophage SenM-STM1 | IDAC deposit 060820-03; |
| Bacteriophage SenM-STM23 | IDAC deposit 060820-04; |
| Bacteriophage SenS-STM47B | IDAC deposit 060820-05; |
| Bacteriophage SenM-M7 | IDAC deposit 060820-06. |

It is the object of the present invention to provide an effective and safe antibacterial formulation for treating infections caused by *Salmonella* spp. particularly *infantis, typhimurium*, Mbandaka, Worthington, Anatum, Livingstone, Manhattan, Bredeney, Agona, I1,4[5]),12:i:-, Sandiego serovars in non-human animals. The bacteriophages comprising this formulation have not been previously described in the state of the art, therefore, the formulation as well as the method for administering said formulation constitute new and effective alternatives to meet the proposed objectives.

It is part of the scope of the invention, the use of the described antibacterial formulation as a medicament useful for the prevention and treatment of infectious diseases caused by *Salmonella* spp. particularly serovars *infantis, typhimurium*, Mbandaka, Worthington, Anatum, Livingstone, Manhattan, Bredeney, Agona, I1,4[5]),12:i:-, Sandiego in non-human animals. In particular, when said infectious disease corresponds to infections by *Salmonella* and said serovars.

Another scope of the present invention is to provide an antibacterial formulation capable of preventing the emergence of antibiotic resistant bacteria and the accumulation of residual antibiotic in animals when treating infections caused by *Salmonella* spp. particularly *infantis, typhimurium*, Mbandaka, Worthington, Anatum, Livingstone, Manhattan, Bredeney, Agona, I1,4[5]),12:i:-, Sandiego serovars.

In a preferred embodiment, the antibacterial formulation is administered as a veterinary formulation to the animal orally, in format or presentation as a liquid or powder (solid).

It is part of the scope of the invention, the presentation of the formulation comprising bacteriophages as a formulation in liquid form for disinfecting environments, surfaces and equipment, in particular, environments and surfaces. In particular, for the disinfection of environments and surfaces in contact with chickens during breeding, slaughter and processing. In the case of equipment, this includes textile, plastic and rubber equipment, such as shoe covers, breastplates, aprons, caps, caps, gloves or other.

It was confirmed that the bacteriophages that comprise the antibacterial formulation are safe for their veterinary application and administration, since they correspond to bacteriophages with lytic activity, which do not present codifying sequences for virulence factors, integrases or antibiotics resistance. Additionally, the analyses allow establishing that there are no indications that support the probability of transduction of bacterial DNA by the phages.

These characteristics demonstrate their safety for inclusion in a veterinary product. The bacteriophages that comprise the formulation comply with what is requested in the general genomic information guidelines described by the US Food and Drug Administration for the approval of use of a bacteriophage mixture (Philipson et al., 2018).

In addition, morphological and biochemical properties were identified that confirm that the bacteriophage has excellent acid and heat resistance. Particularly, when the effect of pH on bacteriophage lytic activity was evaluated, bacteriophages SenM-STM1, SenM-M7, SenM-STM2, and SenM-L8 maintained their stable antimicrobial activity in the acidic pH range. Bacteriophage SenM-STM1 presented activity at pH 2, while SenM-STM23 presented detectable antimicrobial activity in the pH range of 1 and 2. In addition, SenM-STM47B presented stable activity between the pH range above 4.

With respect to the stability of the bacteriophages described in the present invention at different temperature ranges, the 5 bacteriophages described exhibit stable antimicrobial activity as low as 4° C. SenM-M7 and SenS-STM47B bacteriophages also showed stable antimicrobial activity after exposure to 60° C., while SenS-STM47B bacteriophage maintains its stable antimicrobial activity at −20° C.

All these characteristics allow to establish that the bacteriophages composing the formulation proposed in the present invention are safe and suitable for use in phage therapy, and for environmental and surface application.

In the antibacterial formulation described as part of the scope of the invention, the bacteriophages are found in the formulation in amounts or concentrations of 0.001-1000 PFU/CFU, preferably 0.001-0.1 PFU/CFU, being defined as the ratio of bacteriophage to bacterial load. In a preferred form of the invention, the bacteriophages are in amounts or concentrations $9 \times 10^6$ to $9 \times 10^9$ PFU/mL. Wherein bacteriophages are found in equal or different concentrations when it corresponds to a mixture of two or more.

In the antibacterial formulation described as part of the scope of the invention, pH stabilizers, vehicles and pharmaceutically acceptable excipients were selected.

In the case of the vehicle of the formulation, this corresponds to the diluent with which the active principle is administered. Such pharmaceutical vehicles can be sterile liquids, selected from water and oils, including those of animal, vegetable or synthetic origin. In a preferred embodiment, water or aqueous solutions are employed as a vehicle.

Included in the formulation are pharmaceutically acceptable excipients corresponding to substances or compounds that give characteristics to the formulation that ensure the stability, bioavailability, acceptability and ease of administration of the active principle, in this case, bacteriophages. The pharmaceutical and veterinary acceptable excipients of the formulation correspond to preservatives selected from the group of ionic salts, salts from the group of parabens and salts from the group of chelators.

Preservatives acceptable as excipients for the formulation include benzoic acid and benzoates, boric acid and borates, benzyl alcohol, cyclodextrins, benzalkonium chloride, fragrances, fructose, propylene glycol and propylene glycol esters, sodium, sodium salts (sorbates, organic salts such as sodium acetate, sodium butanoate, sodium benzoate, sodium hydroxybenzoate, parabens, sodium methyl-4-hydroxybenzoate, sodium stearate, sodium propionate, sodium propyl-4-hydroxybenzoate, sodium citrate, sodium lactate or sodium salts of organic acids). Also included are chelating preservatives such as trisodium ethylenediamine disuccinate acid, lactic acid, citric acid, ethylene diamine tetraacetic acid (EDTA), phytic acid, among other chelating agents acceptable for pharmaceutical and veterinary use.

It is also part of the formulation of the present invention, pH stabilizer corresponding to those substances or compounds that have the ability to maintain constant pH by adding small amounts of acids or bases to the formulation and maintain its characteristics. Among the pH stabilizers part of the invention, they include without limitation, phosphate salt buffer, citrate buffer (citric acid/sodium citrate), acetate buffer (acetic acid/sodium acetate), benzoate buffer (benzoic acid/potassium benzoate), formate buffer (formic acid/potassium formate), Certipur®, or any pharmaceutical and veterinary acceptable pH stabilizer.

In the antibacterial formulation described as part of the scope of the invention, the bacteriophages and the vehicle, pH stabilizers and/or pharmaceutically acceptable excipient are preferably in a ratio of 1:6. Particularly, the formulation comprises a mixture of bacteriophages and pharmaceutical and veterinary acceptable excipients in a concentration in the range with respect to the final formulation of: pH stabilizers 0.50-1.50% w/v, preservatives 0.50-1.00% w/v, bacteriophages 0.2-0.8% w/v and water to complete 100%.

It is a further object of the present invention to provide a method for preventing or treating infectious diseases caused by *Salmonella* spp. particularly *infantis, typhimurium*, Mbandaka, Worthington, Anatum, Livingstone, Manhattan, Bredeney, Agona, I1,4[5]),12:i:-, Sandiego serovars wherein said method comprises administering the described antibacterial formulation in a non-human animal.

In particular, for breeding animals or cattle, sheep, goats, pigs and poultry. Said method comprises administering the antibacterial formulation comprising the bacteriophages to a non-human animal orally, wherein the human animal is preferably poultry.

The results observed for the proposed formulation regarding its capacity to reduce enteric *Salmonella* in broiler chickens from a farm in the central-south zone of Chile, composed of 10 wards, with a history of prevalence of *Salmonella* spp. higher than 40%, are interesting. The results of the determination of the load of *Salmonella* spp. and *S. infantis* in rectal swabs allow establishing that the bacteriophage formulation reduces the load of *Salmonella* spp. and *Salmonella enterica* serovar *infantis*, with respect to the control without administering the formulation.

When the prevalence of *Salmonella* spp. was determined by the traditional method of shoe covers, it was observed that the formulation also has a decreasing effect on the prevalence of *Salmonella* spp. when detected by the Traditional Method.

It is part of the scope of the invention, a method for preventing or treating infectious diseases caused by *Salmonella* spp. in breeding animals because it comprises administering the antibacterial formulation to a non-human animal orally, wherein, the administration regimen includes at least one dose daily, with a minimum of 3 doses throughout the breeding.

Definitions

The following are definitions of terms that allow a complete understanding of this invention. The definitions comprise clear scientific and technical terms. Any changes in these definitions will be indicated within the text.

The term "bacteriophage" or "phage" refers to a type of virus whose host cells are specifically bacteria. In the case of the invention, the host bacteria correspond to one or more strains of *Salmonella* spp. For purposes of the invention, the term may also be used to refer to fragments of such viruses or assemblies including these parts, whose functional activity is similar to that of employing them in their entirety.

The term "lytic activity" refers to the property of a virus to cause lysis in its host cell.

The term "phage therapy" refers to the use of bacteriophages to treat a bacterial infection, using those that are specific for that infection.

The term "mix" or "mixture" or "combination" of phages refers to a mixture containing at least two bacteriophages distinct from each other, which constitutes the active ingredient of the antibacterial formulation.

The term "antibacterial formulation" refers to a composition which is directed to the prevention or treatment of infections caused by bacteria. For the purposes of the invention, "antibacterial" is understood as the total elimination, decrease or reduction of the bacterial population or bacterial load.

The unit "PFU/mL" (Plaque Forming Unit) is a measure of the number of lysis halos present on a bacterial culture plate per unit volume of virus, where theoretically each halo is formed by the presence of a single virus. In this case, it is a unit for quantifying the number of phage viral particles capable of lysing host cells.

The term "bacterial infection" refers to the invasion of these pathogenic microorganisms into a host, resulting in disease.

The term "serovar" refers to a group of bacterial species that share functional surface structures (antigens) that allow them to infect their host cells and trigger pathogenesis.

The term "effective amount", for purposes of the invention, refers to an adequate concentration of the bacteriophage or bacteriophages comprising the antibacterial formulation for performing the treatment of the disease, within a designated range. This "effective amount" may vary according to the bacterial strain to be targeted, the subject to be administered, or the type of formulation to be prepared.

The term "pharmaceutically acceptable vehicle or excipient" refers to any component, regardless of its nature, that allows the correct administration of the bacteriophages in the species to be treated. Examples of pharmaceutical and veterinary acceptable excipients are preservatives selected from ionic salts, chelating salts and parabens, pH stabilizers among others.

In the case of a pH stabilizer, this corresponds to a substance, compounds or mixture of compounds that have the ability to maintain a constant pH when small amounts of acids or bases are added.

The term "vehicle" refers to a diluent, adjuvant or excipient with which the active ingredient is administered. Such pharmaceutical vehicles can be sterile liquids, such as water and oils, including those of animal, vegetable or synthetic origin. Water or aqueous solutions of saline solution are preferably used as a vehicle.

Meanwhile, the term "veterinary use" refers to its application only in non-human animals.

The term "treatment" or "treat" and its derivatives refers to the care and combating of a disease or the symptoms it causes. For the purposes of the invention, "treatment" is understood as the administration of the formulation in order to eliminate, ameliorate, stabilize or ameliorate the symptoms of the disease, or to kill or reduce the bacterial population causing the disease.

In the present invention, when referring to "non-human animal" these correspond to farm animals or livestock, including but not limited to cattle, sheep, goats, swine and poultry.

The terms "prevention" or "prevent" and its derivatives refer to reducing the probability of contracting a disease. In this case, it refers to reducing or avoiding the spread of a bacterial infection by administering the formulation.

FIGURES

FIG. 1: Resistance profile of bacterial strains. a) Acquired resistance of *Salmonella enterica* strains from the repository (in silico). The resistance classification (Magiorakos et al., 2012) is indicated on the right: (S) Susceptible to all categories, (R) Resistant to between 1 or 2 categories and (MR) Multiresistant, i.e. resistant to 3 or more categories. b) Prevalence of acquired resistance to antibiotic categories of *Salmonella enterica* isolates. The graph and the first row of the table show the frequency of resistant isolates from an n=119, the following rows indicate the relative frequency of resistance according to serovar.

Figure 2:
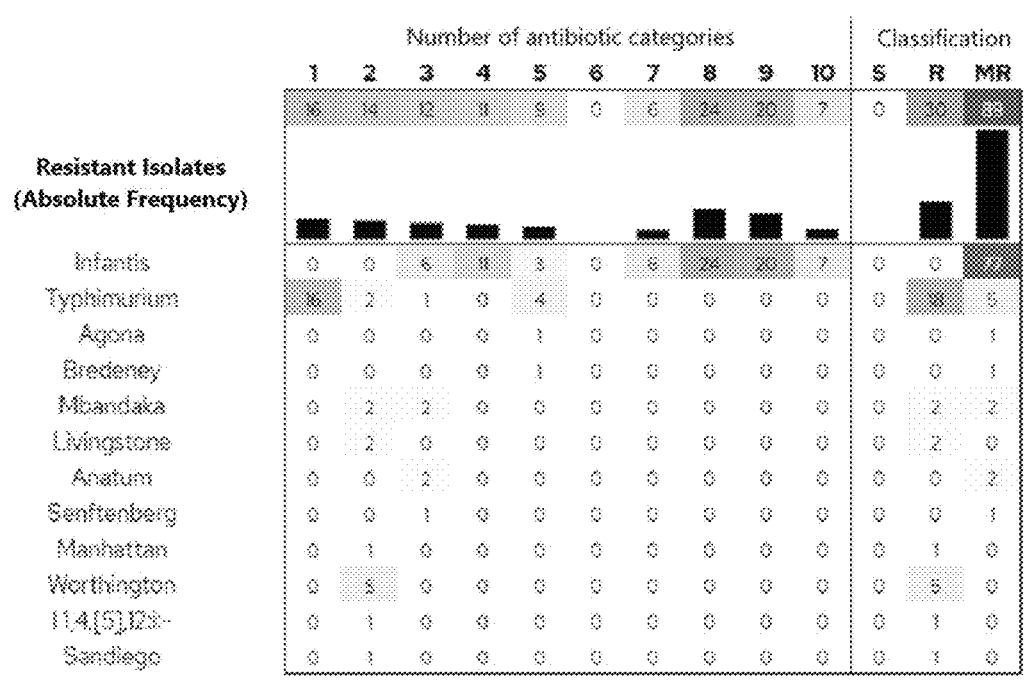

FIG. 2: Resistance profile of *Salmonella enterica* isolates. Describes the resistance profile of *Salmonella* isolates according to the method of Magiorakos (2011): (S) Susceptible to all categories, (R) Resistant to between 1 or 2 categories and (MR) Multiresistant, i.e. resistant to 3 or more categories. The graph and the first row of the figure indicate the absolute frequency considering the isolates of an n=119 and in the following rows, it is indicated according to the isolate serovar.

Figure 3:
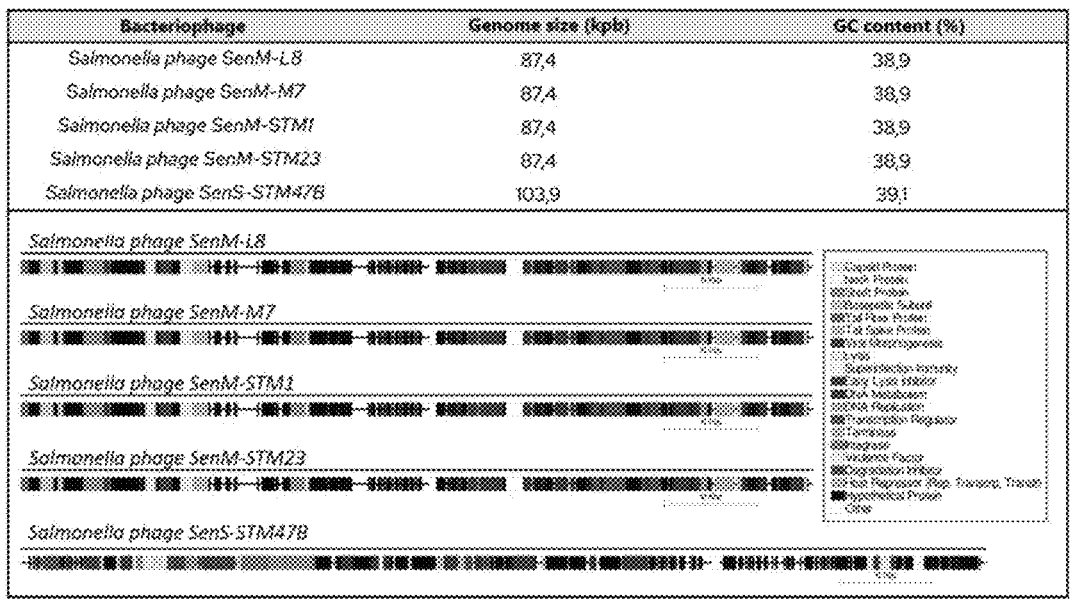
Figure 3:
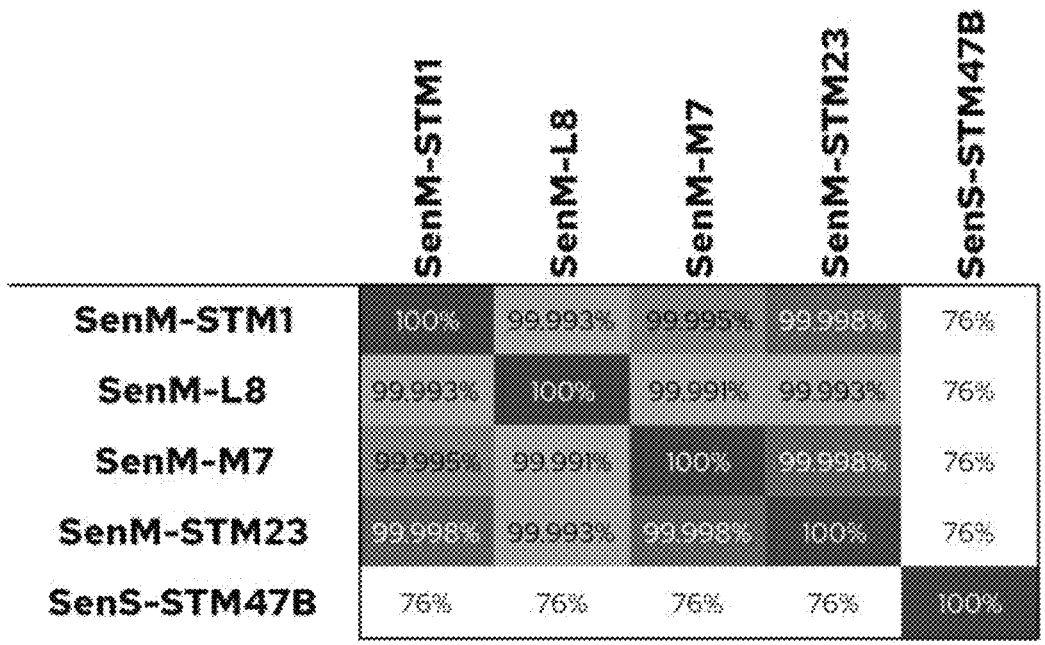

FIG. 3: Comparative analysis of bacteriophage genomes. a) The size, GC % and genomic map of the five bacteriophages are described. The coding regions are represented as bars which were assigned a color according to their biological function and the non-coding regions were assigned only horizontal lines. b) An identity matrix of the five bacteriophages obtained by sequence alignment using Blast is presented. The darker grayscale indicates greater identity in the sequences.

Figure 4:
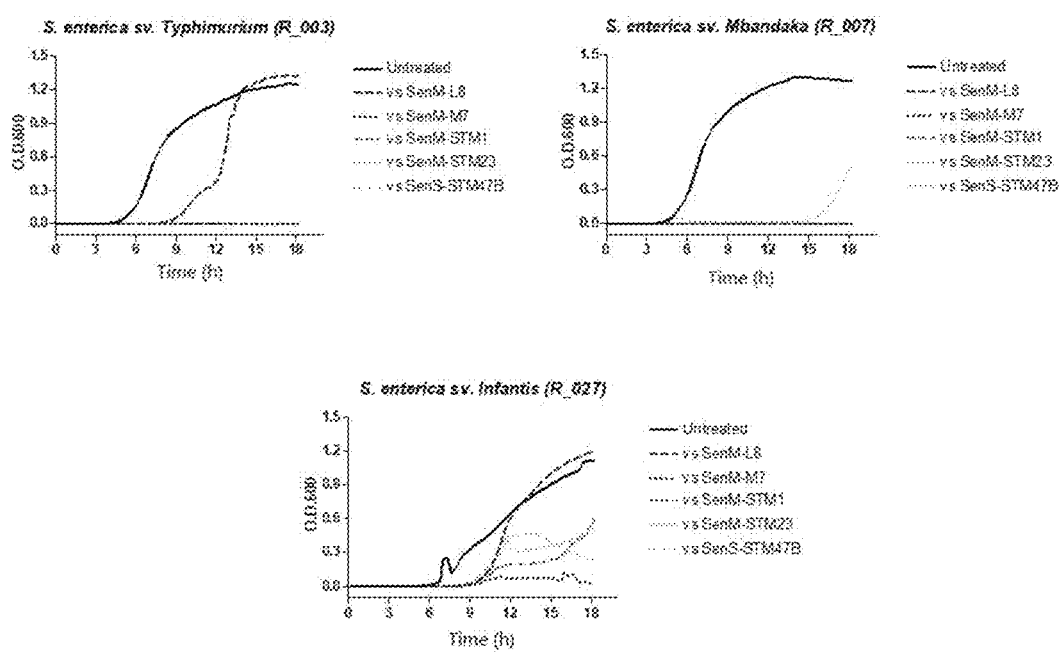

FIG. 4: Growth inhibition effect of five bacteriophages on repository enteric *S. enterica*. The graphs depict the curves obtained after measurement of OD600 over the culture time of each bacteriophage in the repository. The black line indicates the control without bacteriophage treatment, the rest of the dotted lines indicate each of the bacterial assays with the different bacteriophages.

Figure 5:
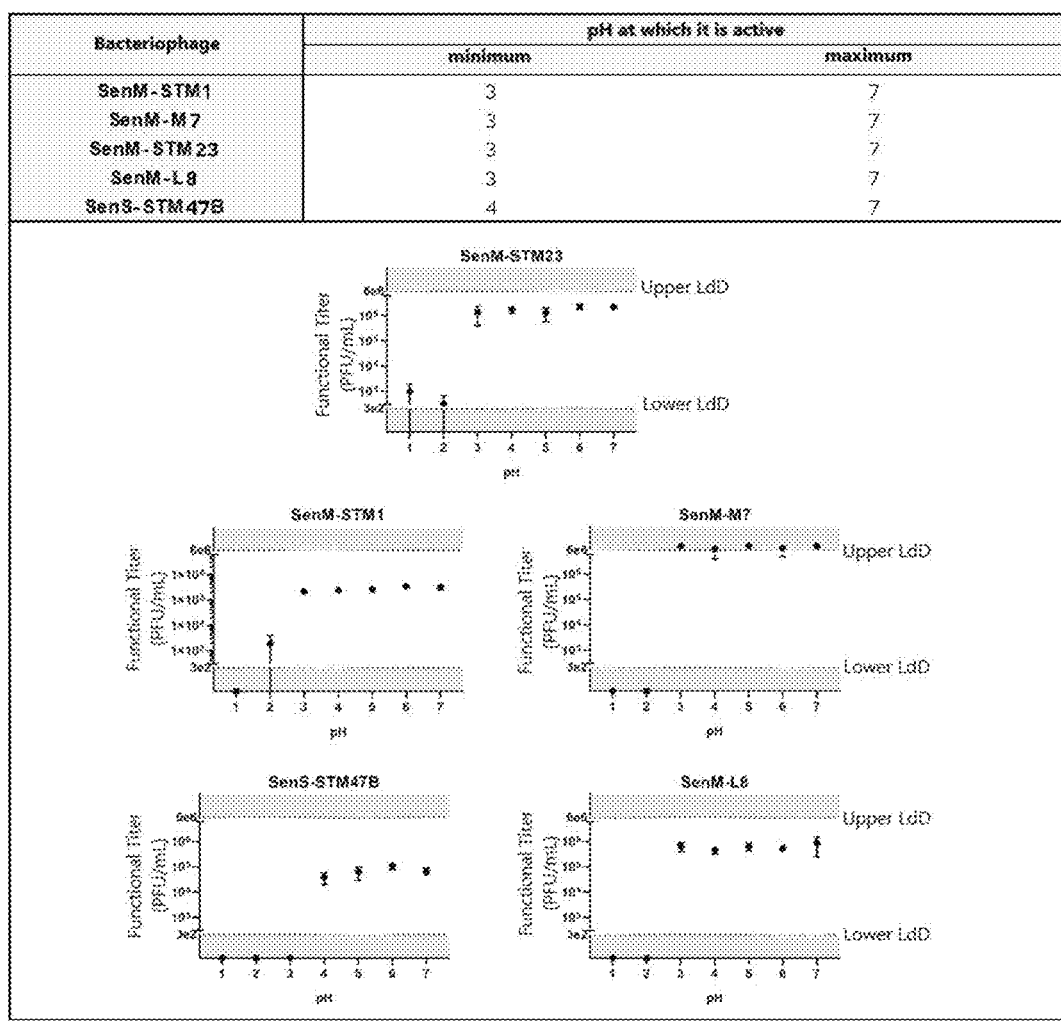

FIG. 5: Bacteriophage activity profile under different acidity conditions. The circles above the white area in each graph represent the mean titer (n=3) and the error bars indicate the standard deviation. The dotted lines indicate the detection limits and the gray area represents the values above and below these limits.

Figure 6:
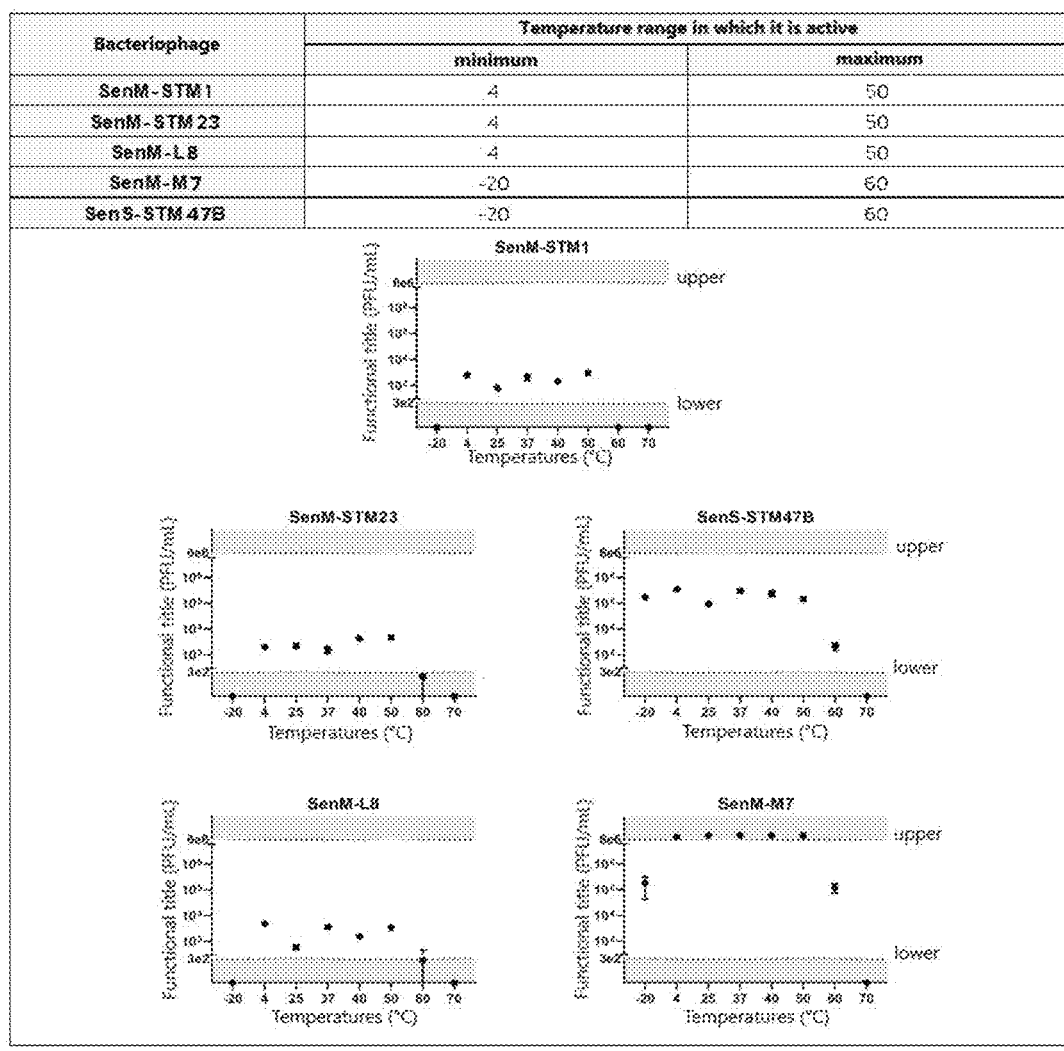

FIG. 6: Activity profile of bacteriophages at different temperatures. Activity profile of candidate bacteriophages at different temperature conditions. The circles above the white area in each graph represent the average titer (n=3) and the error bars indicate the standard deviation. The dotted lines indicate the detection limits and the gray area represents the values above and below these limits.

Figure 7:
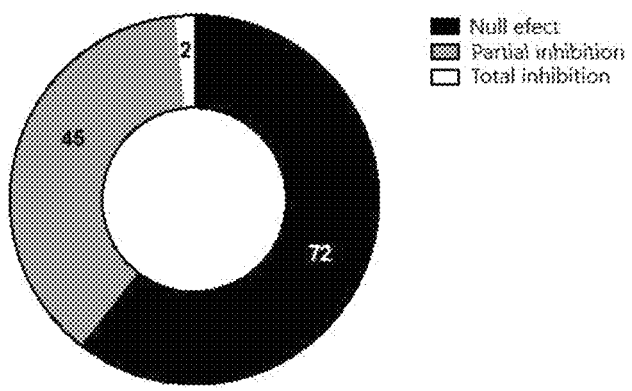
Figure 7:
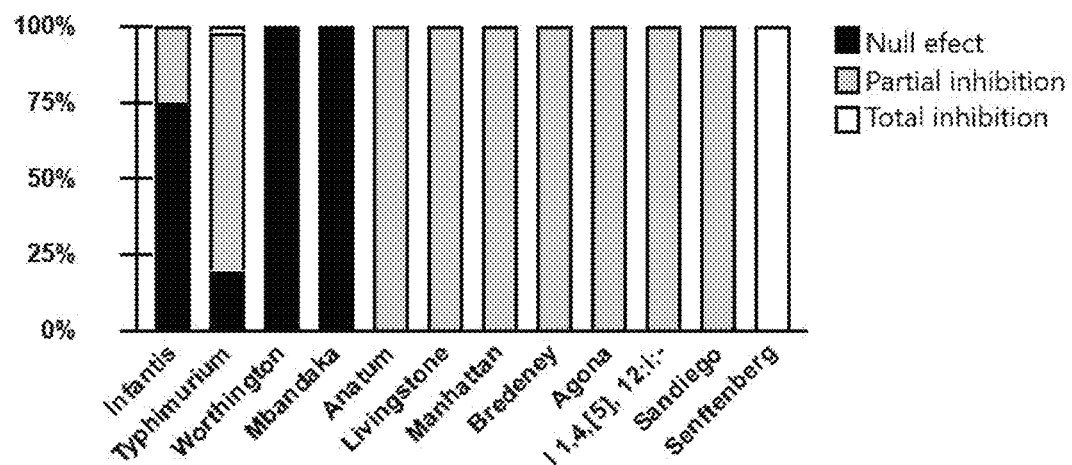
Figure 7:
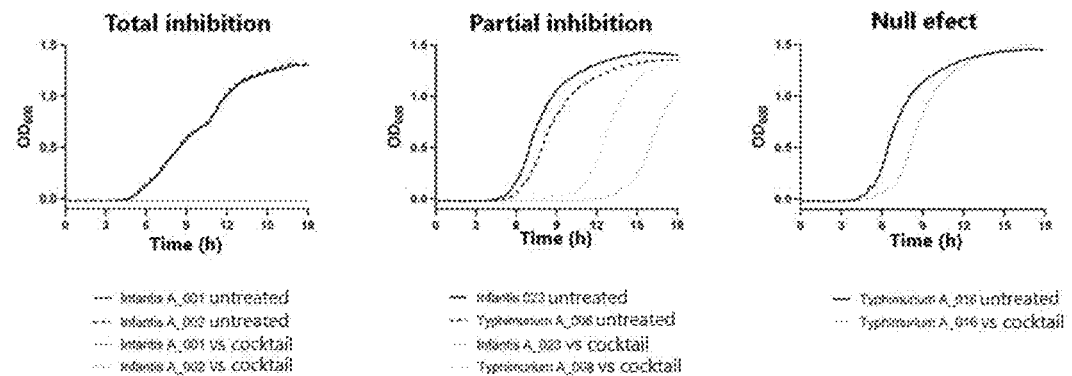

FIG. 7: Host range of the bacteriophage cocktail against the 119 *S. enterica* isolates. a) Proportion of isolates according to the type of effect: Total Inhibition implies growth inhibition above 85%, Partial Inhibition, between 15% and 85% and Null Effect below 15%. b) Distribution of the type of antimicrobial effect, according to serovar. c) Examples of inhibitory effect on the growth of *S. enterica* isolates, according to type of effect.

Figure 8:
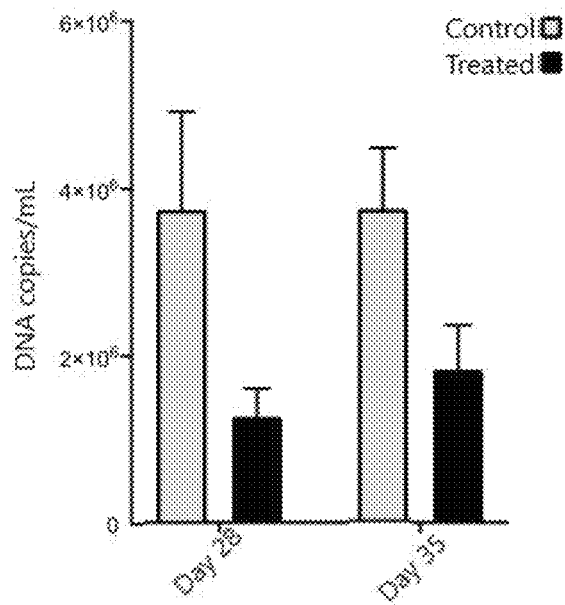
Figure 8:
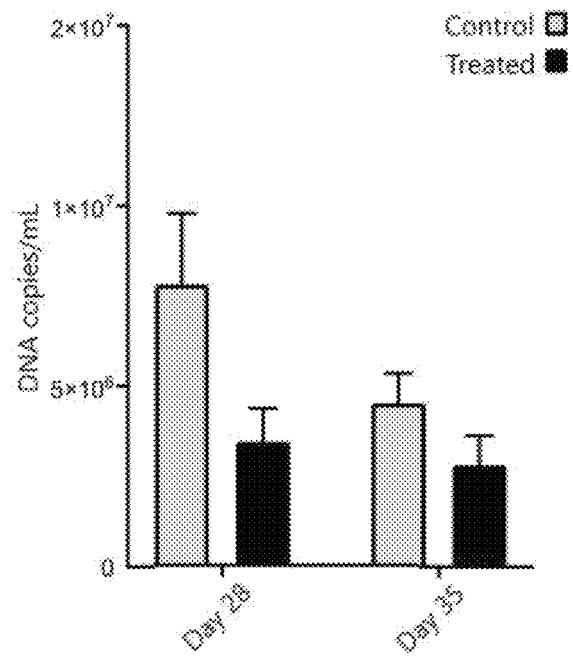

FIG. 8: *Salmonella* spp., *S. infantis* and *S. typhimurium* load in rectal swabs. The graph presents the average and SEM of the determination of *Salmonella* load in rectal swab samples, which were analyzed by qPCR on days 28 and 35. a) indicates the load of *Salmonella* spp. and b) indicates the load of *S. infantis*. The load is indicated as DNA copies/mL. Gray bars indicate control group samples and black bars indicate treated group samples.

Figure 9:
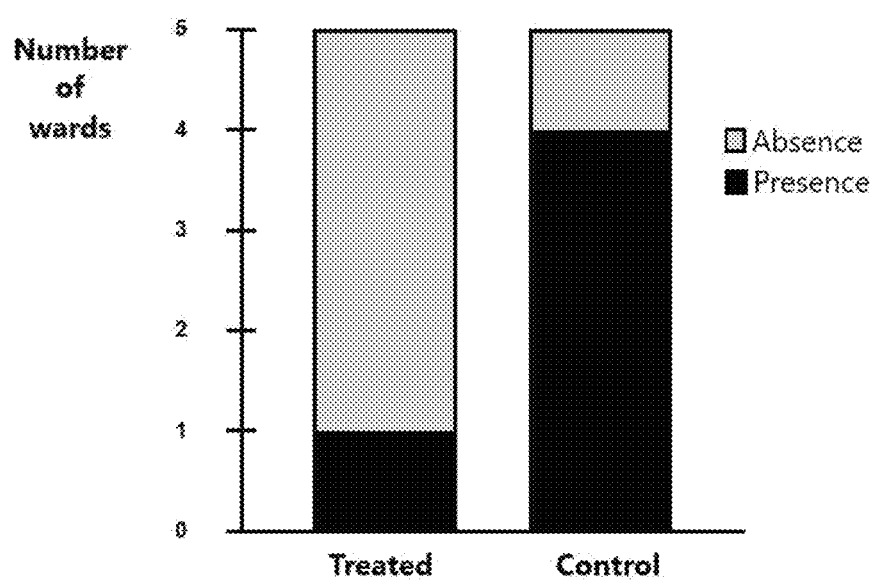

FIG. 9: Prevalence of *Salmonella* spp. evaluated by traditional method in samples of shoe covers. The graph shows the prevalence of *Salmonella* in footwear covers by the traditional method. The number of wards is indicated and the presence of *Salmonella* is shown in black and the absence of *Salmonella* in gray.

EXAMPLES

Example 1. Obtaining *Salmonella* Strains and Preparation of Bacteriophages 1.1 Obtaining *Salmonella* Strains.

*Salmonella* strains were acquired from the repository of the ISP (Instituto de Salud Pública, Chile) and the American Type Culture Collection (ATCC, USA) (Table 1). In addition, strains isolated from footwear covers and cloacal swabs were obtained from different industrial broiler farms in Chile, particularly broiler hatcheries or broiler breeding halls. These samples were analyzed for the presence of *Salmonella* spp. according to the Screening Method VIDAS® EASY SLM AFNOR BIO 12/16-09/05 or Method for detection of mobile *Salmonella* spp. in feces and crawling swabs ISO 6579:2002/Amd 1.

TABLE 1

*Salmonella enterica* strains acquired from ISP (Chile) and ATCC.

| Serovar | Repository | Repository Code | Internal ID |
|---|---|---|---|
| Typhimurium | ISP | ISP 3143-11 | Typhimurium R_003 |
| Mbandaka | ISP | ISP 3663-11 | Mbandaka R_007 |
| *Infantis* | ATCC | ATCC 51741 | *Infantis* R_027 |

Of those samples that tested positive for the presence of *Salmonella*, a saturated culture was prepared and inoculated into a tube containing 5 mL of TSB, incubated overnight at 37° C. After the incubation period, these saturated cultures were seeded on ChromID *Salmonella* agar (Biomerioux), XLD agar, or DMLIA agar, incubated, and then the colonies were isolated and stored according to the manufacturer's instructions. In addition, the growth conditions of each of the strains were determined, the linear range and the equation for the quantification of the microbiological titer were identified by measuring OD600. The strain that presented the widest range of quantification is *typhimurium* R_003, allowing quantification between $2.3 \times 10^7$ and $1.1 \times 10^9$ CFU/mL, *infantis* R_027 (between $1.7 \times 10^7$ and $5.0 \times 10^8$ CFU/mL) and finally, Mbandaka R_007 (between $1.2 \times 10^7$ and $4.8 \times 10^8$ CFU/mL).

On the other hand, the results indicate that a total of 119 *S. enterica* strains were isolated from broiler breeding sectors, most of these isolates (64.7%) were identified as serovar *infantis*, with *typhimurium* (19.3%) being the second most prevalent serovar. Worthington, Mbandaka, Anatum and Livingstone serovars were found in a smaller proportion, representing between 1.7% and 4.2% of the total, respectively. The serovars with the lowest frequency (0.9%) detected were Agona, Bredeney, 11,4,[5],12:i:-, Manhattan, Sandiego and Senftenberg, with one isolate of each.

1.2 Preparation of Bacteriophage Suspension.

Initially, a mixture of bacteriophages was prepared in TSB medium. This mixture was inoculated with a saturated culture of *Salmonella* spp. strain, which was selected as host. This co-inoculum was incubated for a period of 18 hours at 37° C. with a constant agitation of 200 rpm.

To purify the bacteriophages from the culture, it was centrifuged at 3200 g for 5 minutes to separate the bacteria and large particles. The supernatant was filtered using a 0.45 μm porosity polyethersulfone (PES) membrane.

To obtain the viral titer, 15 mL of TSB with agar was placed and incubated at room temperature for a period of 30 minutes. In parallel, 3 mL of TSB with agar was mixed with 1 mL of saturated host bacterial culture and 1 mL of TSB, and poured onto the previously prepared TBS plate.

Subsequently, serial dilutions of bacteriophage concentrate were prepared in potencies of 10. These dilutions were inoculated onto the TSB plate for 18 hours at 37° C. After the incubation period, the viral microbiological titer was determined by counting lysis plaque forming units (PFU).

Example 2: Determination of Nucleotide Sequences from Bacterial and Viral DNA and their Characterization 2.1. DNA Extraction.

Bacterial and viral DNA was purified using the Thermo Fisher extraction kit, following the manufacturer's recommendations. DNA quantification was performed by fluorimetry in the Qubit Fluorometer 3.0 kit (Thermo Fisher), with the reagents and parameters recommended by the manufacturer.

2.2. Library Synthesis.

With the DNA obtained in the previous step, double-stranded DNA libraries were prepared using the Illumina library preparation kit, with paired-end partitions. The size profile of the libraries was verified using the Fragment Analyzer kit (Agilent), according to the manufacturer's instructions. DNA was quantified by fluorimetry using the Qubit Fluorometer 3.0 (Thermo Fisher), according to the manufacturer's instructions.

2.3 Genetic Characterization of Viral DNA and Bacterial DNA.

A DNA sequence analysis was performed on the samples obtained in point 1.2. For this purpose, bacterial genomic DNA sequencing and analysis of *Salmonella* isolates was performed.

2.4. Bacterial Genomes Characterization.

From the bacterial genomes obtained in the previous point, different in silico analyses were performed for typing according to essential gene sequences, identification of virulence factors and resistance genes, and determination of the serovar of the bacteria.

The analyses allowed the identification of the prevalence of *Salmonella enterica* serovars in the samples. These results are shown in Table 2.

TABLE 2

Prevalence of serovars identified in *S. enterica* strains isolated from broiler houses.

| Serovar | No of Isolated from Broiler chickens | Percentage (%) |
| --- | --- | --- |
| *Infantis* | 77 | 64,.7 |
| Typhimurium | 23 | 19.3 |
| Worthington | 5 | 4.2 |
| Mbandaka | 4 | 3.4 |
| Anatum | 2 | 1.7 |
| Livingstone | 2 | 1.7 |
| Agona | 1 | >0.9 |
| Bredeney | 1 | >0.9 |
| I1, 4, [5], 12: i: - | 1 | >0.9 |
| Manhattan | 1 | >0.9 |
| Sandiego | 1 | >0.9 |
| Senftenberg | 1 | >0.9 |

Genes associated with microbial resistance were identified. The results indicated that the repository strains present genes conferring acquired resistance to aminoglycosides. In addition, Mbandaka R_007 and *infantis* R_027 exhibited resistance to fluoroquinolones. No predicted genes conferring resistance to the other 13 resistance categories were observed. Because all four strains showed acquired resistance (predicted in silico) to one or two categories, they were classified as resistant bacteria (FIG. 1a). With respect to the isolates, all showed acquired resistance (predicted in silico) to aminoglycosides, of which 82% of the isolates also showed resistance to fluoroquinolones. In addition, the presence of resistance to 9 categories of antibiotics was identified, where most of the isolates had resistance genes to tetracyclines (71%) and phenicols (53%). There was no resistance to first or second generation cephalosporins, carbapenemics, cephamycins or glycylcyclines (FIG. 1b).

On the other hand, it was possible to observe the presence of differences in the resistance acquired by the different serovars. Resistance to penicillins was observed mainly in serovars *infantis* and *typhimurium* (in the latter in a low proportion). Only *infantis* serovar showed resistance to monobactam and extended-spectrum cephalosporins, with a prevalence of 74%. The only serovars that showed resistance to polymyxins were Senftenberg and Mbandaka (FIG. 1b).

On the other hand, the isolates showed acquired resistance between 1 and 10 of the 15 antibiotic categories. Of these isolates, 75% were classified (according to the method of Magiorakos et al., 2012) as multidrug resistant (resistance to 3 or more categories), the remaining 25% as resistant (between 1 and 2 categories). None of the isolates showed susceptibility to all categories. In addition, variability was observed in the number of categories between serovars and within the same serovar. In the case of *infantis*, resistance to between three and ten categories was detected, so that all isolates were classified as multidrug-resistant. In the other serovars, resistance to between one and five categories was identified (FIG. 2).

2.5. Viral Genomes Characterization.

To characterize the viral genomes, different in silico analyses were performed to describe the type of viral DNA packaging, determine the viral DNA replication cycle, detect the presence of coding sequences for integrases, virulence factors and bacterial resistance genes, and establish the taxonomic identity of the bacteriophages.

The five bacteriophages obtained correspond to the order Caudovirales, which are characterized by being tailed, overstranded DNA bacteriophages. Additionally, five bacteriophages (SenM-L8, SenM-M7, SenM-STM1 and SenM-STM23) belong to the Myoviridae family, which are characterized by having long and contractile tails. Finally, the five bacteriophages belong to the subfamily Ounavirinae and the genus Felixonavirus, with the exception of SenS-STM47B, which belongs to the genus Tequintavirus and is characterized by a long, non-contractile tail.

Bacteriophages SenM-L8, SenM-M7, SenM-STM1 and SenM-STM23 have identical genome size, GC content and genetic structure (FIG. 3a). On the other hand, SenS-STM47B, the only Siphoviridae, has a larger genome size and GC content, and the ordering of its genes is different. The genome map of the bacteriophage genomes shows that there are no integrases or virulence factors, a necessary feature in bacteriophages used in phage therapy. When comparing the genomes of the five bacteriophages, a trend similar to that shown by the genomic map is observed: there is a high identity among the bacteriophages of the Myoviridae family (over 99.991%) and these differ significantly from SenS-STM47B, of the Siphoviridae family (76% identity) (FIG. 3b).

Example 3: In Vitro Lytic Activity on *Salmonella* Strains and Bacteriophages Characterization 3.1. Evaluation of the Inhibitory Effect on Bacterial Growth.

A culture of the bacterium of interest was mixed in TSB medium having OD600=0.3, and diluted 1:105 with bacteriophage suspensions to an initial MOI greater than 105 PFU/CFU or by bringing the mixture to a final volume of 200 μL with TSB medium. The mixtures were added to a 96-well plate and incubated for 18 hours at 37° C. using EPOCH 2 spectrophotometry equipment with continuous orbital shaking. The OD600 was recorded every 10 minutes. The antimicrobial effect of the mixture was determined by comparing the ratio of the area under the growth curve in the presence and absence of the bacteriophage. Null effect (N): inhibition up to 15% of growth. Partial inhibition (P): between 15% and 85%. Total inhibition (T): reduction over 85%.

In this assay, 5 bacteriophages (isolated from wastewater from the city of Santiago, Chile) were identified as having antimicrobial activity against some of the *S. enterica* repository strains. Bacteriophages present different activity profiles, however, they present a similar range of activity against at least 3 of the 4 bacteria in the repository (Table 3).

TABLE 3

Host range of 6 bacteriophages isolated from wastewater with lytic activity on *Salmonella enterica* repository strains.

| Bacteriophage ID | Growth inhibition with respect to bacteria without bacteriophage treatment | | | |
|---|---|---|---|---|
| | Typhimurium (R_003) | Mbandaka (R_007) | *Infantis* (R_027) | Amplitude |
| SenM-L8 | 36% | 100% | 12% | 4 |
| SenM-M7 | 100% | 100% | 93% | 3 |
| SenM-STM1 | 100% | 100% | 71% | 4 |
| SenM-STM23 | 100% | 100% | 62% | 4 |
| SenS-STM47B | 100% | 94% | 60% | 4 |

The activity of the repository bacteria is affected by each of these bacteriophages. There is a high percentage inhibition on the growth of Mbandaka R_007 and *typhimurium* R_003, except in the case of phage SenM-L8 which after approximately 4 hours the growth of *typhimurium* R_003. The effect on the growth of *infantis* R027 is varied and in general, the inhibition of *Enteritidis* R_006 growth is low (up to 39%) (FIG. 4).

Also, the similarity of the five bacteriophages to others bacteriophages already reported was determined. The bacteriophages of this invention are different from those reported in the state of the art, in the results a maximum similarity of 87.8% was obtained. The bacteriophage that is most similar to SenM-L8, SenM-M7, SenM-STM23 and SenM-STM1 is *Salmonella* Phage Si3 and the most similar to SenS-STM47B is a bacteriophage from *Shigella* SS 1 (Table 4).

TABLE 4

Similarity of five bacteriophages of the invention with respect to previously reported bacteriophages.

| Bacteriophage | Closest bacteriophage | Coverage[1] | Identity | Similarity[2] |
|---|---|---|---|---|
| SenM-L8 | *Salmonella* phage Si3 (NC_041922.1) | 92.0% | 95.5% | 87.8% |
| SenM-M7 | *Salmonella* phage Si3 (NC_041922.1) | 92.0% | 95.5% | 87.8% |
| SenM-STM1 | *Salmonella* phage Si3 (NC_041922.1) | 92.0% | 95.5% | 87.8% |
| SenM-STM23 | *Salmonella* phage Si3 (NC_041922.1) | 92.0% | 95.5% | 87.8% |
| SenS-STM47B | *Shigella* phage SSP1 (NC_047881.1) | 88.0% | 94.4% | 83.1% |

[1]Best alignment result in Blastn's "nr" database, GenBank code in parentheses.
[2]Similarity defined as the product of the identity calculated on the basis of the coverage of the search sequence.

Finally, other characteristics of the bacteriophages were predicted and it was observed that they present characteristics that indicate that they are suitable for use in phage therapy, in terms of biological safety. All of them present a lytic replication cycle (essential for phage therapy). No elements related to transduction potential such as integrases, recombination sites, genes of bacterial origin, virulence or resistance genes were found (Table 5)

TABLE 5

Biosafety of the five bacteriophages.

| Bacteriophage | Replication cycle | Integrase | attL/attR sites | Bacteria gene | Virulence gene | Resistance gene | Suitable for phage therapy |
|---|---|---|---|---|---|---|---|
| SenM-L8 | Lytic | Absence | Absence | — | — | — | — |
| SenM-M7 | Lytic | Absence | Absence | — | — | — | — |
| SenM-STM1 | Lytic | Absence | Absence | — | — | — | — |
| SenM-STM23 | Lytic | Absence | Absence | — | — | — | — |
| SenS-STM47B | Lytic | Absence | Absence | — | — | — | — |

3.2. Evaluation of Bacteriophage Stability Under Acidic Conditions.

An aliquot of 10 µL of concentrated bacteriophage culture was taken and diluted in 250 µL of acid saline (NaCl 0.9% w/v pH 1, 2, 3, 4, 5, 6 and 7) and incubated for 4 hours at 37° C. After incubation, 750 µL of neutralizing solution (NaHCO$_3$ 0.53% w/v+HCl 12.3 mM) was added. The mixture was then incubated for 20 minutes at 4° C. and the viral titer was determined as described in section 1.2.

The results of this assay showed that three bacteriophages (SenM-STM1, SenM-M7 and SenM-L8) exhibit stable activity between pH 3 and 7 for a period of 4 hours. In addition, SenM-STM1 showed detectable but reduced antimicrobial activity upon exposure to pH 2 and SenM-STM23 for which reduced activity was detected at pH 1 and 2, being the bacteriophage with the widest range of activity under acidic conditions. On the other hand, SenM-STM47B showed a smaller range of activity, remaining stable between pH 4 and 7. It should be noted that the differences in the level of activity of the bacteriophages are due to the initial concentration of each one in the assay (FIG. 5).

3.3. Evaluation of Bacteriophage Stability at Different Temperatures.

An aliquot of 10 µL of bacteriophage culture was taken at a concentration of 5×10$^7$ or higher and diluted in 250 µL of acid saline (NaCl 0.9% w/v pH 5.5). The solution was incubated for a period of 4 hours at −20, 4, 25, 37, 40, 50, 60 and 70° C. After incubation, 750 µL of neutralizing solution (NaHCO$_3$0.53% w/v+HCl 12.3 mM) was added. Subsequently, this solution was incubated at 4° C. for 20 minutes and the viral titer was determined as indicated in point 1.2

Results indicate that the antimicrobial activity of the bacteriophages remained stable when exposed to temperatures between 5 and 50° C. In addition, SenM-M7 and SenS-STM47B showed reduced activity after exposure to 60° C. Interestingly, SenS-STM47B maintained stable activity at −20° C. It is worth mentioning, that the difference in titer between bacteriophages is due to the fact that the initial concentration of each was different. To detect reduced activity in the SenM-STM1, SenM-STM23 and SenM-L8 bacteriophages, it is necessary to increase the concentration in the assay, approaching the upper limit of detection (FIG. 6).

Example 4: Formulation of Bacteriophages with Lytic Activity on Salmonella enterica Isolates The combination of bacteriophages: bacteriophage SenM-L8 (IDAC deposit 060820-01), bacteriophage SenM-STM1 (IDAC deposit 060820-03), bacteriophage SenM-STM23 (IDAC deposit 060820-04), bacteriophage SenS-STM47B (IDAC deposit 060820-05) and bacteriophage SenM-M7 (IDAC deposit 060820-06) are prepared with pharmaceutical and veterinary acceptable excipients, according to the following ratios or concentration ranges (Table 6)

TABLE 6

Formulation components and proportions.

| Formulation component | Proportion (% w/v) |
|---|---|
| pH stabilizers | 0.5-1.5 |
| Preservatives | 0.5-1.0 |
| Bacteriophages | 0.2-0.8 |
| Water | Quantity to complete 100% |

Example 5. Evaluation of the Efficacy of the Formulation Comprising the Bacteriophage Mixture on Salmonella enterica Isolates 5.1. Determination of Minimal Inhibitory MOI (MIM).

The growth inhibitory effect was assessed by mixing bacterial cultures diluted 1:105 with OD$_{600}$=0.3 with suspensions of bacteriophages at a MOI$_{initial}$ of 10$^{-3}$, 10$^{-2}$, 10$^{-1}$, 10$^0$, 10$^1$, 10$^2$, y 10$^3$ PFU/CFU, or bring the mixture to a final volume of 200 µL with TSB medium. As with the antimicrobial activity assay, the suspensions were transferred to a 96-well plate and incubated for a period of 18 hours at a temperature of 37° C. in EPOCH 2 with continuous orbital shaking, determining OD600 every 10 minutes. The antimicrobial effect of each bacteriophage was determined mathematically by comparing the area under the growth curve in the presence and absence of bacteriophage. The MIM was determined as the minimum MOI evaluated in the assay that presented bacterial growth inhibition over 85% (total inhibition).

The five bacteriophages were then used in a formulation, considering that each one is unique, suitable for phage therapy and with antimicrobial activity on Salmonella. The results showed that the formulation presents antimicrobial activity on 98.3% of the Salmonella enterica isolates obtained from broiler farms. A total growth inhibition of 60.5% (infantis, typhimurium, Mbandaka, Worthington serovars) and a partial inhibition of 37.8% (Anatum, Livingstone, Manhattan, Bredeney, Agona, I1,4[5]),12:i:-, Sandiego serovars). In only 2 of the 119 isolates (1.7%), one of Senftenberg serovar and one of typhimurium serovar, no effect on bacterial growth was observed (FIGS. 7a and 7b).

The isolates on which the cocktail had a total growth inhibition effect belong to infantis serovar (75% of these), typhimurium (20%) and all Worthington and Mbandaka isolates. These four serovars are the most prevalent among the strains obtained from broiler houses. For the other serovars, with the exception of Senftenberg, at least partial growth inhibition was observed (FIGS. 7b and 7c).

In addition, the Minimum Inhibitory MOI (MIM) to achieve total inhibition (above 85%, MIM85) and 50% growth inhibition (MIM50) was determined to be different for each repository strain (Table 7). For *infantis* R_027 MIM85 occurs at an MOI of 0.1 PFU/CFU, i.e. at a ratio of one bacteriophage per ten bacteria, whereas, to reduce bacterial growth by half, 1,000 times fewer bacteriophages than bacteria were required (MOI 0.001 PFU/CFU). The best performance was achieved against *typhimurium* R_003 since both MIM values are equivalent and correspond to the lowest concentration tested (MOI=0.001 PFU/CFU). A low MOI of 0.001 PFU/CFU is required to inhibit the growth of Mbandaka R_007 by half, however, a much higher MOI of 1 PFU/CFU is necessary to achieve total inhibition.

Considering the maximum load of *Salmonella* in the cecum chicken ($9 \times 10^6$ copies/cecum), would require, in the worst case scenario (MIM85=1 PFU/CFU) a dose of $9 \times 10^6$ PFU of cocktail per chicken to achieve total inhibition of *infantis*, *typhimurium* and Mbandaka serovars. This dose is compatible with the concentrations achievable at the bacteriophage production level (over $10^9$ PFU/mL per bacteriophage, data not shown).

TABLE 7

Minimal inhibitory MOI of bacteriophage formulation to inhibit the growth of *Salmonella enterica*.

| Repository Strain | MOI (PFU/CFU) | |
|---|---|---|
| ID | $MIM_{85}$ | $MIM_{50}$ |
| *Salmonella enterica* sv. Infantis R_027 | 0.1 | 0.001 |
| *Salmonella enterica* sv. Typhimurium R_003 | 0.001 | 0.001 |
| *Salmonella enterica* sv. Mbandaka R_007 | 1 | 0.001 |

Example 6: Evaluation of the Efficacy of Bacteriophages in the Reduction of *Salmonella enterica* in Broiler Chickens This evaluation was carried out on a farm in south-central Chile, consisting of 10 wards, with a history of *Salmonella* spp. prevalence above 40%.

The results of these trials are presented below

Determination of *Salmonella* Spp. and *S. infantis* Load in Rectal Swab.

The bacterial load was determined by qPCR from rectal swabs. The results showed that there are significant differences in the load of *Salmonella* spp. between the "treated" and "control" conditions, with the load being higher in the control group samples at 28 and 35 breeding (p=0.012431; p=0.032947 respectively) (t-test, alpha=0.05). These results can be seen in Table 8 and FIG. 8a.

TABLE 8

*Salmonella* spp. bacterial load from rectal swab samples.

| | Control | | | Treated | | |
|---|---|---|---|---|---|---|
| Breeding day | Average (DNA copies/mL) | SD | n | Average (DNA copies/mL) | SD | n |
| 28 | $3.75 \times 10^6$ | $8.55 \times 10^6$ | 53 | $1.28 \times 10^6$ | $3.34 \times 10^6$ | 98 |
| 35 | $3.76 \times 10^6$ | $5.05 \times 10^6$ | 48 | $1.84 \times 10^6$ | $4.83 \times 10^6$ | 83 |

The load of *Salmonella enterica* serovar *infantis* showed significant differences between the "control" and "treated" groups, with the "control" group showing a higher load on day 28 (p=0.024505) than the "treated" group (t-Test, alpha=0.05). The samples on day 35 of breeding showed no differences between the study groups (Table 9; FIG. 8b).

TABLE 9

Bacterial load of *Salmonella enterica* serovar Infantis from rectal swab samples.

| | Control | | | Treated | | |
|---|---|---|---|---|---|---|
| Breeding day | Average (DNA copies/mL) | SD | n | Average (DNA copies/mL) | SD | n |
| 28 | $7.82 \times 10^6$ | $1.25 \times 10^7$ | 40 | $3.47 \times 10^6$ | $8.31 \times 10^6$ | 81 |
| 35 | $4.54 \times 10^6$ | $5.36 \times 10^6$ | 42 | $2.82 \times 10^6$ | $6.04 \times 10^6$ | 55 |

Determination of Prevalence of *Salmonella* Spp. by the Traditional Method of Shoe Covers.

On day 27-29 of breeding, footwear covers were sampled and analyzed by the ISO 6570:2002/Amd1:2007 method. The results indicate that the prevalence of *Salmonella* spp. is lower in the "treated" group when compared to the "control" group (FIG. 9). This means that the treatment decreased the prevalence of *Salmonella* spp. when detected by the Traditional Method.

REFERENCES

Jamal, M., Bukhari, S. M., Andleeb, S., Ali, M., Raza, S., Nawaz, M. A., . . . & Shah, S. S. (2019). Bacteriophages: an overview of the control strategies against multiple bacterial infections in different fields. Journal of basic microbiology, 59(2), 123-133.

Magiorakos, A. P., Srinivasan, A., Carey, R. B., Carmeli, Y., Falagas, M. E., Giske, C. G., . . . & Monnet, D. L. (2012). Multidrug-resistant, extensively drug-resistant and pan-drug-resistant bacteria: an international expert proposal for interim standard definitions for acquired resistance. Clinical microbiology and infection, 18(3), 268-281.

Modi, R., Hirvi, Y., Hill, A., & Griffiths, M. W. (2001). Effect of phage on survival of *Salmonella enteritidis* during manufacture and storage of cheddar cheese made from raw and pasteurized milk. Journal of food protection, 64(7), 927-933.

Philipson, C. W., Voegtly, L. J., Lueder, M. R., Long, K. A., Rice, G. K., Frey, K. G., . . . & Bishop-Lilly, K. A. (2018). Characterizing phage genomes for therapeutic applications. Viruses, 10(4), 188.

Whichard, J. M., Sriranganathan, N., & Pierson, F. W. (2003) Suppression of *Salmonella* growth by wild-type and large-plaque variants of bacteriophage Felix 01 in liquid culture and on chicken frankfurters. Journal of food protection, 66(2), 220-225.

The invention claimed is:

1. An antibacterial formulation comprising a mixture of bacteriophages having lytic activity against strains of *Salmonella* spp. comprising:
   a) an effective amount of specific bacteriophages:
   Bacteriophage SenM-L8 IDAC deposit 060820-01, Bacteriophage SenM-STM1 IDAC deposit 060820-03, Bacteriophage SenM-STM23 IDAC deposit 060820-04, Bacteriophage SenS-STM47B IDAC deposit 060820-05, and Bacteriophage SenM-M7 IDAC deposit 060820-06, wherein the bacteriophages are at concentrations of $9 \times 10^6$ to $9 \times 10^9$ PFU/mL; and
   b) an acceptable vehicle, buffer and excipients, wherein the acceptable excipients are preservatives of anionic salts group, of parabens group and of chelators group.

2. The antibacterial formulation according to claim 1, wherein the bacteriophages with respect to the total mass in the formulation are included in the range of 0.2-0.8% w/v.

3. The antibacterial formulation according to claim 1, wherein in the acceptable the vehicle is water.

4. The antibacterial formulation according to claim 1, wherein the excipients and components with respect to the total mass in the formulation are included according to the following % w/v:
   pH stabilizers 0.5-1.5% w/v
   Preservatives 0.5-1.0% w/v
   Bacteriophages 0.2-0.8% w/v
   Water Amount to complete 100% w/v 5. The antibacterial formulation according to claim 1, wherein the formulation formulated as a veterinary formulation.

6. The antibacterial formulation according to claim 1, wherein the formulation is formulated as a veterinary oral formulation.

7. The antibacterial formulation according to claim 1, wherein the formulation is formulated as a veterinary formulation for oral administration in liquid or powder form.

8. The antibacterial formulation according to claim 1, wherein the formulation is formulated as an environmental, surface and equipment disinfection liquid formulation.

9. A method for treating infectious diseases caused by *Salmonella* spp. comprising using the antibacterial formulation according to claim 1.

10. A method for treating infections produced by *Salmonella* serovars *Infantis, Typhimurium*, Worthington, Mbandaka, Anatum, Livingstone, Manhattan, Bredeney or Agona comprising using the antibacterial formulation according to claim 1.

11. A method for treating infections caused by *Salmonella* serovars *Infantis, Typhimurium*, Worthington, Mbandaka comprising using the antibacterial formulation according to claim 1.

12. A method for treating infections caused by *Salmonella* in a non-human or farm animal comprising applying the antibacterial formulation according to claim 1 to the non-human or farm animal.

13. A method for treating *Salmonella* infections in poultry comprising applying the antibacterial formulation according to claim 1 to the poultry.

14. A method for decreasing bacterial load of *Salmonella* on surfaces and equipment comprising applying the formulation according to claim 1 on surfaces and equipment.

15. A method for decreasing bacterial load of *Salmonella* on poultry breeding, transfer, slaughter and processing surfaces and equipment comprising applying the formulation according to claim 1 to the poultry breeding, transfer, slaughter and processing surfaces and equipment.

* * * * *